United States Patent
Dister et al.

[11] Patent Number: 6,053,047
[45] Date of Patent: Apr. 25, 2000

[54] DETERMINING FAULTS IN MULTIPLE BEARINGS USING ONE VIBRATION SENSOR

[75] Inventors: Carl J. Dister, North Olmsted; Edward J. Tompkin, Cuyahoga Falls; Kenneth A. Loparo, Chesterland, all of Ohio

[73] Assignee: Allen-Bradley Company, LLC, Milwaukee, Wis.

[21] Appl. No.: 09/163,111

[22] Filed: Sep. 29, 1998

[51] Int. Cl.[7] .................................................. G01M 13/04
[52] U.S. Cl. .............................................. 73/593; 73/660
[58] Field of Search ........................... 73/593, 659, 660; 702/35, 56, 39

[56] References Cited

U.S. PATENT DOCUMENTS

| | | | |
|---|---|---|---|
| 4,352,293 | 10/1982 | Kurihara et al. | 73/593 |
| 4,479,389 | 10/1984 | Anderson et al. | 73/593 |
| 4,931,949 | 6/1990 | Hernandez et al. | 73/593 |
| 4,965,513 | 10/1990 | Haynes et al. . | |
| 5,049,815 | 9/1991 | Kliman . | |
| 5,109,700 | 5/1992 | Hicho | 73/660 |
| 5,602,757 | 2/1997 | Haseley et al. . | |

OTHER PUBLICATIONS

"Comments on Rolling Element Bearing Analysis"; by Ronald L. Eshleman, et al.; Vibrations; vol. 13; No. 2; Jun. 1997; pp. 11–17.

*Primary Examiner*—John E. Chapman
*Attorney, Agent, or Firm*—Himanshu S. Amin; John J. Horn; Alexander M. Gerasimow

[57] ABSTRACT

A diagnostic system includes a vibration sensor mounted on a machine which has vibration-generating components having different vibration characteristics with respect to a common sensor. The vibration sensor measures vibrations and sends vibration signals to a diagnostic module for evaluation of the signals. The diagnostic module has software for processing the vibration signals. From a known natural frequency of a vibration-generating component, the diagnostic module measures the amplitude of the vibration signal at more than one harmonic frequency of the known natural frequency and compares the amplitudes to amplitudes at adjacent harmonic frequencies. When a relatively large amplitude is found at a harmonic frequency, that is a harmonic frequency near a resonant frequency of the physical path between the vibration sensor and the vibration-generating component, the diagnostic system can then analyze the shape and magnitude of the vibration signal around that harmonic frequency to evaluate whether each of the vibration-generating components is healthy, broken or about to break.

13 Claims, 10 Drawing Sheets

DETERMINING FAULTS IN MULTIPLE BEARINGS USING ONE VIBRATION SENSOR

FIELD OF THE INVENTION

The invention described below generally relates to a system for diagnosing the health of a dynamoelectric machine, and more particularly, to a system and method for analyzing vibration signatures to predict and to detect changes in the condition of various parts of a dynamoelectric machine.

BACKGROUND OF THE INVENTION

Today's machines are relied upon to operate with minimal attention. Many industrial and commercial facilities operate hundreds or even thousands of machines concurrently, many of which are integrated in a large interdependent process or system. However, although maintenance procedures are becoming increasingly efficient, at any time at least a small percentage of the machines are prone to failure.

For example, machines having moving parts, such as bearings, are subject to constant friction that result in wear. Unfortunately, however, most wear sites are concealed in the machine's assembled state. In particular, bearing damage due to wear from inadequate lubrication, shock or lubricant contamination may not be immediately apparent absent gross damage and/or failure. Thus, it is difficult to monitor wear rates and to prevent excessive wear on internal components of a machine.

Vibration analysis is an established nonintrusive technique for measuring the health of mechanical components in rotating machines. Every rotating machine exhibits a characteristic vibration signature which varies with the design, manufacture, application and wear of each component. Vibration may be generated by machine bearings including, for example, the bearing races, balls and ball races, misalignment of gears, motors, or shafts, and imbalance of rotors, gears, pistons and fans. Analysis of a machine's vibration signature is valuable for reducing unscheduled down time, reducing turnaround time, minimizing periodic disassembly of a machine for inspection and greatly reducing the probability of catastrophic and unexpected machine failure.

A machine's vibration signature is composed of the sum of the vibration signals produced by and/or transmitted through each component of the machine. The vibration signals produced by a component include forcing frequencies that vary with the rotational speed of the machine. For example, the forcing frequencies for a bearing include those of the inner race, the outer race and the ball track, and can be calculated as a function of the rotational velocity, the ball diameter, the pitch diameter, the contact angle and the number of balls. The forcing frequencies are sometimes referred to as the critical frequencies. The health of a particular component can be analyzed by considering the shape and magnitude of the vibration signals at the critical frequency or at harmonics of the critical frequency.

Dynamoelectric machines such as motors generally have a shaft rotatably connected to the rest of the machine via at least two bearings, one toward either end of the machine. Prior to failure such bearings usually experience a degradation in performance which is accompanied by an increase in vibrations.

Since the bearings may be identical, it is generally difficult to determine from analysis of a vibration signal which of the bearings needs to be replaced when increased vibrations are detected. Thus the machine must be disassembled and more than one bearing examined in order to determine which bearing needs replacement. This disassembly and examination increases the time and expense involved in maintaining such machines.

It will be appreciated that it would be desirable to be able to determine, prior to disassembly, which of the bearings of a rotating machine is the source of irregular vibrations.

SUMMARY OF THE INVENTION

The present invention allows evaluation of the health of specific components of a dynamoelectric machine using a single vibration sensor. The machine has vibration-generating components each having unique vibration characteristics. For example, ball bearings supporting the shaft of a motor may have different numbers of balls. The signal generated by a vibration sensor is analyzed in the vicinity of a frequency or frequencies associated with each of the vibration-generating components. An increase in amplitude at frequencies associated with one of the vibration-generating components indicates a degradation in performance that may require replacement of that particular component.

To measure and analyze the above-mentioned increase in amplitude, the present invention includes a diagnostic system having a vibration sensor mounted on a machine to sense vibrations and an electronic device called a diagnostic module, operatively couple to the vibration sensor, to evaluate the vibrations. Vibration signals from the sensor are sent to the diagnostic module which has software for processing and analyzing the vibration signals.

For example, from known critical frequencies of vibration-generating components of the machine, the diagnostic module can scan a plurality of harmonic frequencies of each of the critical frequencies, measure the amplitude of the vibration signal at each harmonic frequency, and compare the amplitudes to amplitudes at adjacent harmonic frequencies. The diagnostic module can identify frequencies associated with each of the components by scanning for a relatively large increase in amplitude at a harmonic frequency of that component. That means that that harmonic frequency is near a resonant frequency of a transmission path between the vibration sensor and the respective vibration-generating component. The diagnostic system can then analyze the shape and magnitude of the vibration signal around that harmonic frequency to evaluate the health of that vibration-generating component.

The present invention also reduces or eliminates the need for a calibrated hammer and includes a diagnostic device which scans the vibration signature of a machine while the machine is running and provides vibration information for particular components with increased efficiency and with a high signal-to-noise ratio.

According to one aspect of the invention a machine diagnostic system includes a vibration sensor mounted on a machine having two or more bearings with unique vibration characteristics with respect to the sensor, the vibration sensor able to sense a vibration signature, and a processor which is adapted to receive the vibration signature from the vibration sensor. The processor evaluates the vibration signature in the vicinity of frequencies associated with the bearings, to determine the health of the machine at each of the bearings.

According to another aspect of the invention, a method of analyzing the health of a rotating machine includes the following steps: providing the machine with vibration-generating components, at least one of which has vibration characteristics different from the others; obtaining a vibration signature from a vibration sensor connected to the machine; processing the vibration signature; and determining the condition of the components from characteristics of the vibration signature at frequencies associated with each of the components.

According to one embodiment of the invention, the processing step of the method includes scanning a frequency region adjacent to a resonant frequency of a vibration transmission path from one of the components to the vibration sensor, for harmonic frequencies of the components.

According to another embodiment of the invention, the processing step of the method includes determining at least one critical frequency for each of the components of the machine; identifying harmonic frequencies of respective of the critical frequencies; recording the amplitudes of the vibration signature at the harmonic frequencies; and comparing the recorded amplitudes to identify a resonant frequency associated with a sudden increase in amplitude.

According to yet another embodiment of the invention, the providing step of the method includes providing the machine with bearings, at least one of which has different vibration characteristics from the others.

According to another aspect of the invention, a combination dynamoelectric machine and diagnostic system includes a machine having at least two bearings, and a vibration sensor mounted on the machine. The machine and the sensor define a path from each of the bearings to the vibration sensor, each of the paths having an associated resonant frequency. The resonant frequencies associated with the paths are unequal.

According to an embodiment of the invention, the combination machine and diagnostic system includes a processor operatively coupled to the vibration sensor, for receiving a vibration signature from the vibration sensor and evaluating the vibration signature in the vicinity of the resonant frequency to determine the health of the machine.

Another embodiment of the present invention provides for a dynamoelectric machine diagnostic system. The system includes: means for sensing vibrations, said means for sensing vibrations operative to sense vibrations from at least two bearings of a dynamoelectric machine; each bearing having a unique vibration characteristic with respect to the means for sensing vibrations; and means for processing the vibration characteristics, said means for processing the vibration characteristics being able to correspond the vibration characteristics to the respective bearings and to determine the health of each of the bearings.

Still another embodiment of the present invention provides for a dynamoelectric machine comprising at least two bearings rotatably coupled to a shaft, wherein at least one of the bearings has different vibration characteristics than another of the bearings with respect to a common sensor.

Yet another embodiment of the present invention relates to a system for diagnosing an operating condition of a component of a dynamoelectric machine. The system includes: first and second vibrating components operatively coupled to the machine, the first component having a different mechanical path to a vibration sensor than the second component; and a processor operatively coupled to the vibration sensor, the processor processing vibration data relating to the first and second components in order to determine operating states of the components, the processor differentiating vibration information with respect to the components based at least partly on the different mechanical paths.

The foregoing and other features of the invention are hereinafter fully described and particularly pointed out in the claims, the following description and the annexed drawings setting forth in detail one or more illustrative embodiments of the invention, such being indicative, however, of but one or a few of the various ways in which the principles of the invention may be employed.

DETAILED DESCRIPTION OF THE INVENTION

A system and a method of the present invention are described below with reference to the drawings, and initially to FIGS. 1 and 2. The invention relates to a diagnostic system and method for obtaining and using vibration data for machine diagnosis and failure prediction. In particular, the invention relates primarily to a machine diagnostic system and method for analyzing vibration data to determine the condition (i.e., health) of the machine, including the health of individual components of the machine. The invention includes a system and method for analyzing vibration data from a vibration sensor which is connected to a machine, where the machine has two or more vibration-generating components such as bearings, at least one of the vibration-generating components having different vibration characteristics than the others, with respect to the sensor. Analysis of the data allows irregularities in the operation of the machine (i.e., a degradation in health of the machine) to be pinpointed to the individual component, such as a bearing, which is causing the irregularities. Thus a component failure or near-failure, such as deterioration of a bearing, can be readily identified to allow prompt and efficient correction by replacement of the component.

The invention also includes a system and a method for analyzing vibration data while reducing or eliminating the need to mechanically ping the machine to determine a resonant frequency or frequencies of the vibration paths between sources of vibration and a vibration sensor.

In the following paragraphs, the invention is primarily described with respect to an alternating-current (AC) induction motor, however, the invention can be applied to most machines (e.g., motors, pumps, generators, gear boxes, etc.) and/or systems that generate vibrations. In particular the invention can be applied to dynamoelectric machines.

Figure 1:
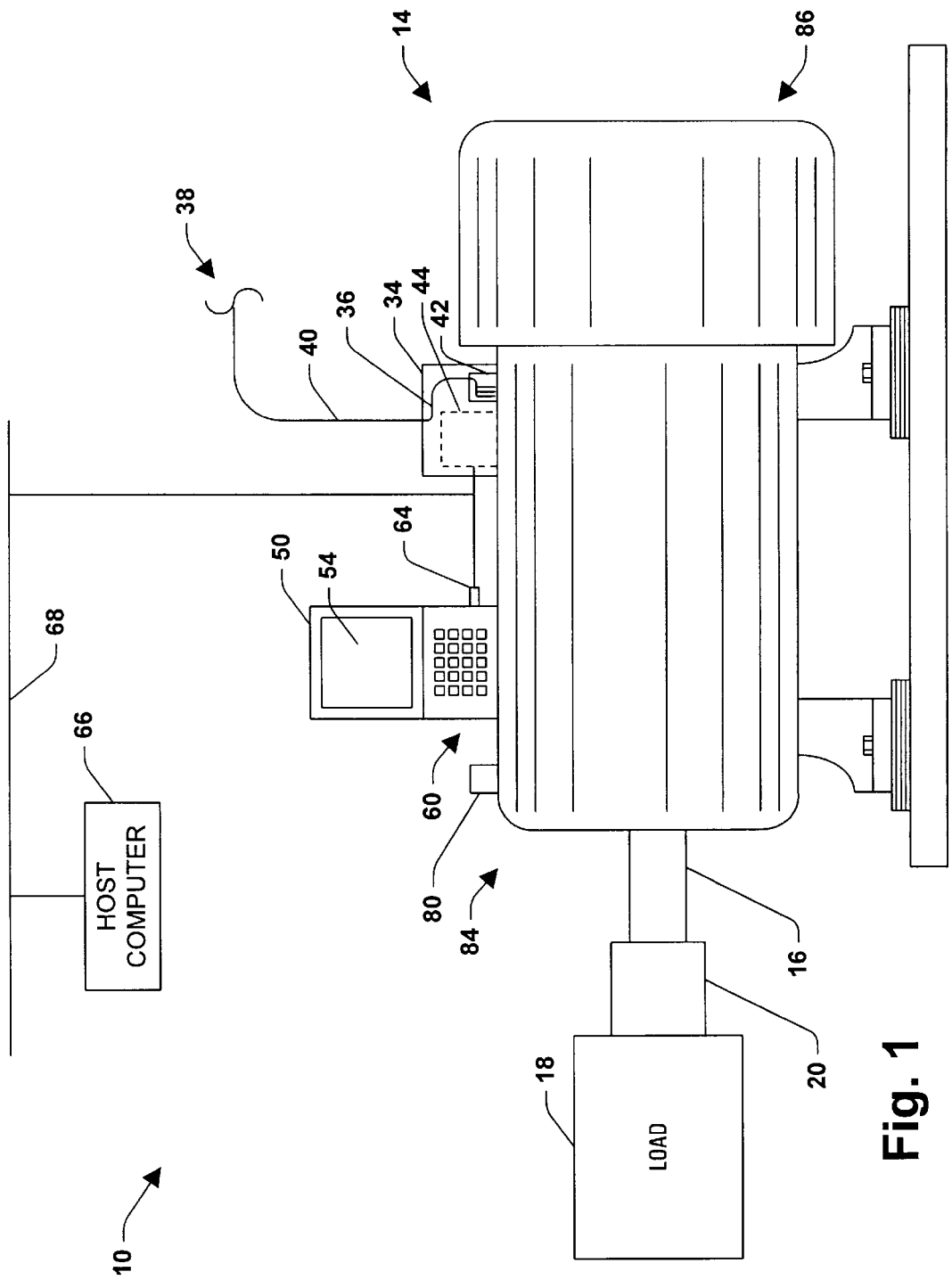
FIG. 1 is a schematic side view of an integrated AC induction motor, interface device and diagnostic module in accordance with one aspect of the invention.
Figure 2:
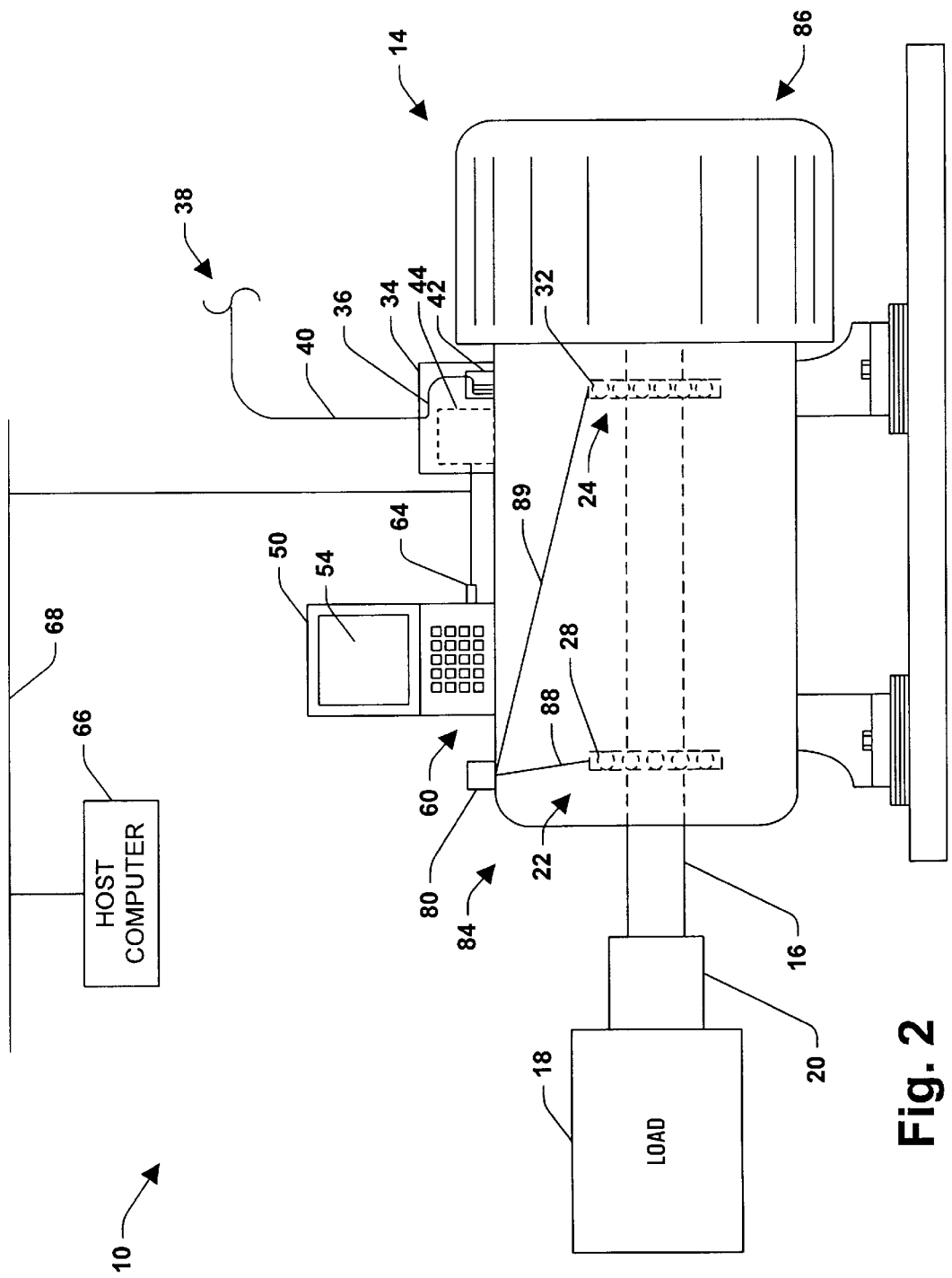
FIG. 2 is a side view of the system of FIG. 1, schematically showing first and second bearings, as well as transmission paths between the bearings and a vibration sensor, within the motor.

An exemplary system 10 according to the invention is shown in FIGS. 1 and 2. A three-phase AC induction motor 14 has a shaft 16, which is connected to a load 18 through a coupling 20. The motor 14 operates at an AC power line frequency of about 60 Hz, although different line frequencies, such as 50 Hz, may be used. The load 18 may be any device or article that is connected and/or is driven by the motor 14 such as a turbine or a pump, for example.

The shaft 16 is coupled to the rest of the motor 14 by a pair of bearings. As shown, the shaft 16 is coupled via the first and second ball bearings 22 and 24 respectively. It will be appreciated that other sorts of bearings (e.g., roller bearings) may alternatively be used to couple the shaft to the rest of the motor. It will further be appreciated that more than two bearings may be employed to rotatably couple the shaft to the rest of the motor.

Figure 3A:
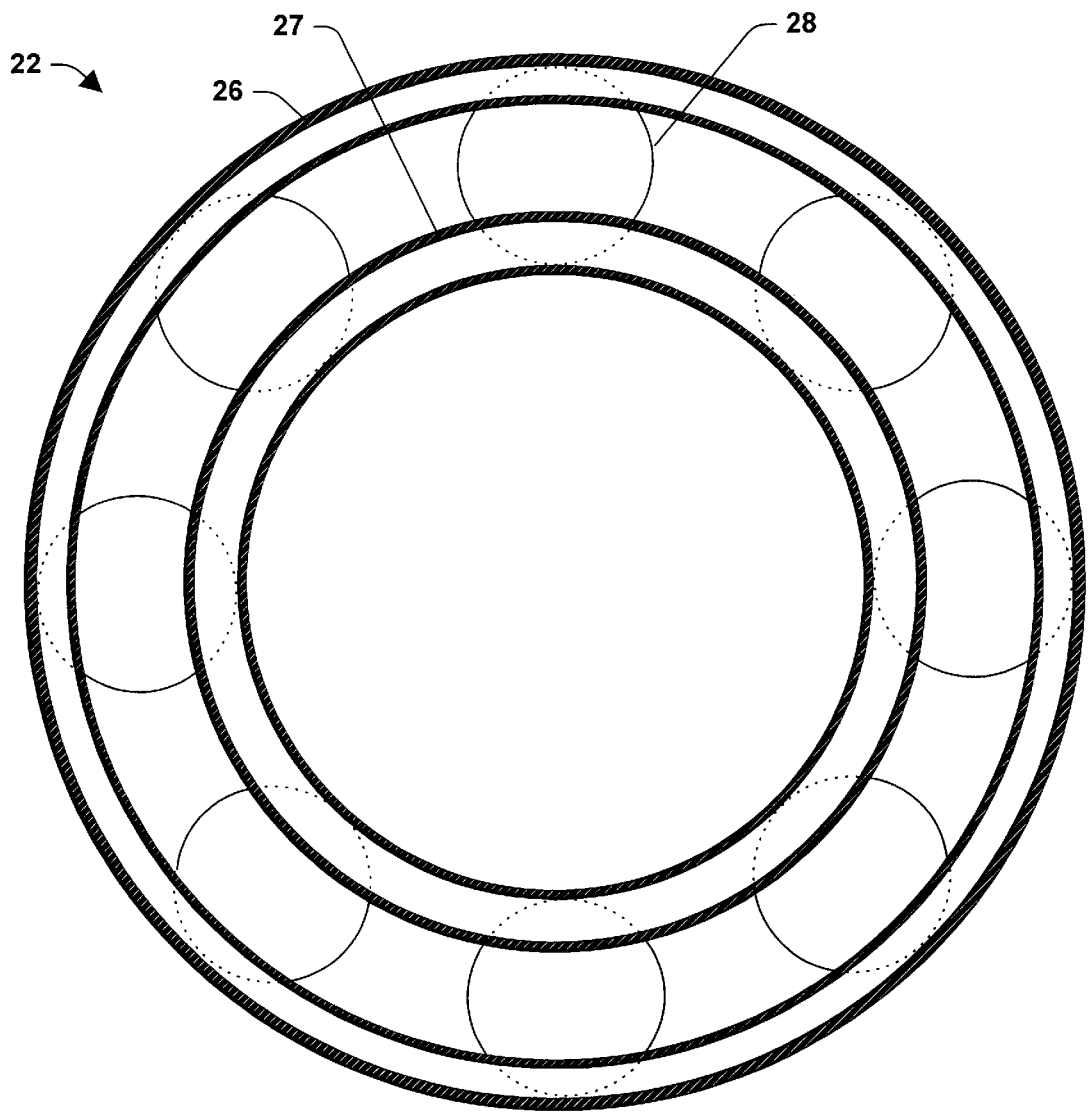
FIGS. 3a and 3b are plan views of the first and second bearings, respectively, of FIG. 2.
Figure 3B:
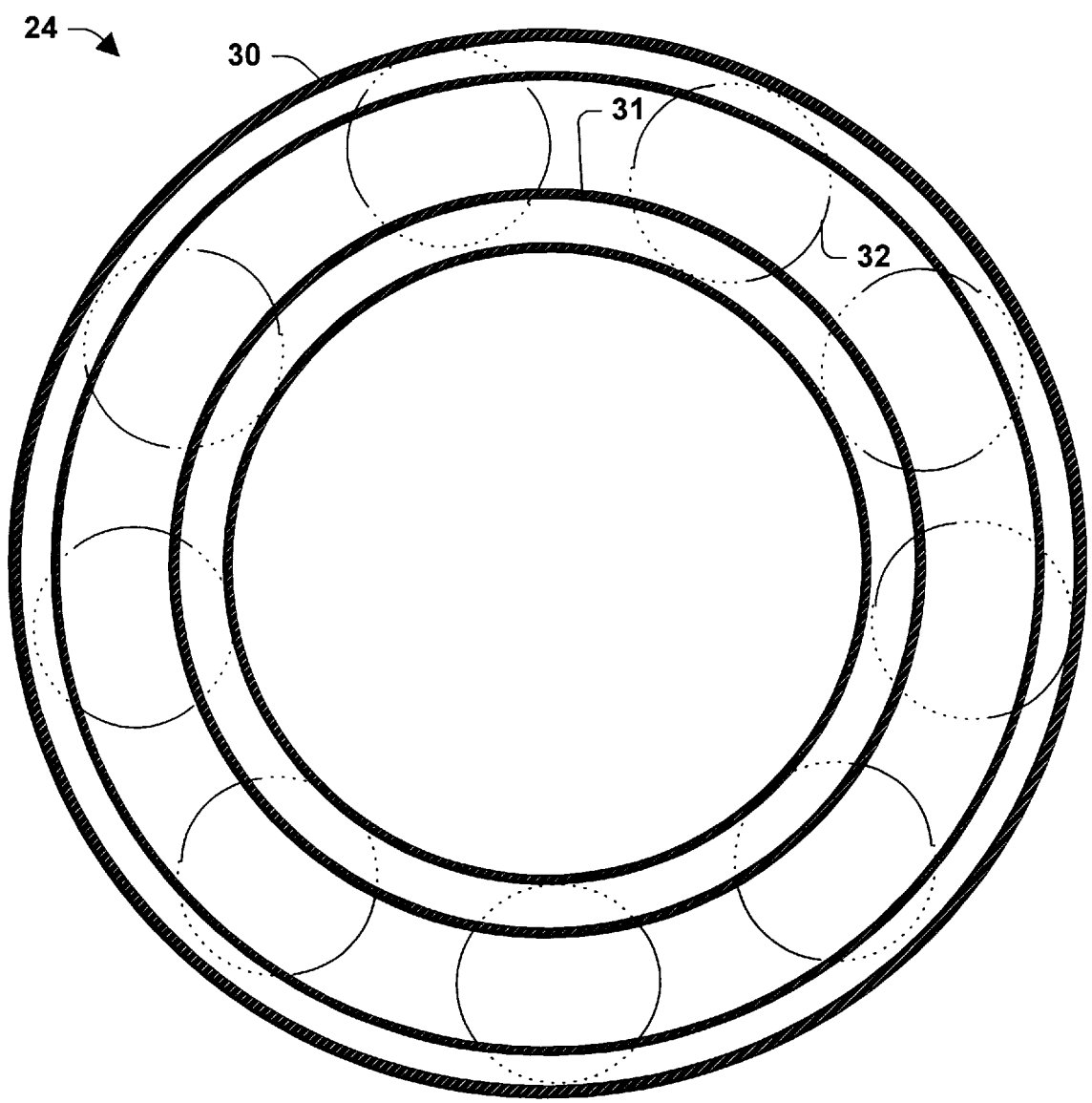

Referring briefly to FIGS. 3a and 3b, the first bearing 22 has a first outer race 26, a first inner race 27, and a first set of balls 28 therebetween. The second bearing 24 similarly has a second outer race 30, a second inner race 31, and a second set of balls 32 therebetween.

The first bearing 22 has different vibration characteristics than the second bearing 24 (e.g., with respect to a common sensor). In the illustrated embodiment this is accomplished by the bearing 22 having a different number of balls than the bearing 24. Thus in FIGS. 3a and 3b, the first bearing 22 has eight balls, while the second bearing 24 has nine balls. Since differences in bearing geometry produce differences in bearing vibrations, this difference in the number of balls produces a different vibration signature (different vibration characteristics for the bearing 22 when compared with the bearing 24.

The number of balls in the bearings is not limited to that of the illustrated embodiment. One skilled in the art may select suitable numbers and sizes of balls for each of the bearings, tailored to the characteristics of the motor and its application, such as the size, type, and operating speed of the motor, and its load.

A difference in vibration characteristics between the two bearings may also be accomplished in other ways besides employing unequal numbers of balls in the two bearings. For example, the sizes of two bearings may be different, with possible differences in the mounting of the bearings on the shaft and/or the rest of the motor. Alternatively or in addition, the geometry of the races may be different between the two bearings. Differences in the lubrication of the two bearings may also produce different vibration characteristics. It will be appreciated that there may be other means of varying the vibration characteristics of the two bearings.

Returning to FIGS. 1 and 2, the motor 14 has an enclosure such as a junction box 34 mounted thereupon. The junction box 34 receives conductors 36 connected to a power source 38 via a conduit 40. The conductors 36 are connected within the junction box 34 to power supply mounts 42 of the motor 14. One of the functions of the junction box 34 is to protect the connections at the power supply mounts 42.

Mounted inside the junction box 34 is a motor diagnostic module 44 which receives and processes data from vibration sensors (described below) relating to the health of the motor 14. Preferably the junction box 34 is suitably weatherproofed to protect the diagnostic module 44 from environmental conditions (e.g., dust, moisture, heat, etc.) experienced by the motor 14. For example, the junction box 34 may include thermal insulation to protect the diagnostic module 44 from heat generated by the motor 14.

The system 10 also includes an interface device 50 coupled to the motor diagnostic module 44. The interface device 50 includes a display 54 for displaying information relating to the operation of the motor 14. The display 54 may be a liquid crystal display (LCD), a cathode-ray-tube (CRT), one or more light emitting diodes (LEDs) or the like. The display 54 displays data or other information relating to the operation of the motor 14. For example, the display 54 may display a set of discrete motor condition indicia such as, for example, fault indicia, caution indicia, and normal operation indicia. Additionally, the display 54 may display a variety of functions that are executable by the motor 14 and/or the diagnostic module 44.

The interface device 50 further includes an input device in the form of a key pad 60, for example, for entering data, information, function commands, etc. in a conventional manner. For example, input information relating to motor status may be input via the key pad 60 for subsequent transmission to a host computer 66. The interface device 50 may use other known input devices including a mouse, a pointer, a touch pad, etc. Furthermore, the interface device 50 may be integrated with the motor diagnostic module 44 and the diagnostic module 44 may carry out substantially all of the functions performed by the interface device 50 and/or the host computer 66. (See FIGS. 9a–9b and the related description below.) Alternatively, the interface device 50 may be located remotely from the motor 14. The interface device 50 also may be portable and alternately connectable to the diagnostic modules of a plurality of machines.

In the illustrated embodiment of the invention the system 10 also includes a network backbone 68. The network backbone 68 may be a hardwired data communication path made of twisted pair cable, shielded coaxial cable or fiber optic cable, for example, or may be wireless or partially wireless in nature. Information is transmitted over the network backbone 68 between the host computer 66, the interface device 50 and the diagnostic module 44. The interface device 50 includes a communications port 64 for interfacing the interface device 50 with the motor diagnostic module 44 and the host computer 66 through a suitable communication link. The communication link preferably adheres to the RS232C or DeviceNet standard for communicating command and parameter information. However, any communication link suitable for carrying out the invention may be employed. Although the invention is directed to vibration analysis, the diagnostic module 44 preferably is capable of analyzing other data, such as current data, voltage data and temperature data to diagnose the health of the motor 14, as described in copending and commonly owned U.S. patent application No. Ser. 08/988,177.

At least one vibration sensor is mounted on the motor 14 to monitor its operation and to collect vibration data from the motor 14. An accelerometer is used as the vibration sensors in the preferred embodiment, however, other types of vibration sensors may be used. For example, proximity detectors may be used as vibration sensors in large machines and/or systems. Since accelerometers sense vibration primarily in one direction, a plurality of accelerometers generally is desirable to detect the vibrations generated in different directions and in different parts of some equipment. Thus, a vibration sensor as described herein may include more than one accelerometer in order to sense all significant vibration directions. Other multiple-axis sensors may be alternatively or additionally employed.

In the preferred embodiment, the motor 14 is equipped with an accelerometer 80 for taking sampled vibration data relating to the operation of the motor 14. As shown in FIGS. 1 and 2, a three-axis accelerometer 80 is located near a load side 84 of the motor 14. It will be appreciated that the accelerometer may alternatively be located elsewhere on the motor 14, such as near a rear side 86 of the motor 14 away from the load side 84. Moreover, the accelerometer 80 may be located within the motor 14 near a bearing for example. However, the invention may be carried out with one or more two-axis and/or single-axis accelerometers. Preferably, the vibration sensor is a laboratory-grade accelerometer such as those manufactured by PCB Piezoelectronics, Inc., Part No. 353B16 and providing 10 mv/g. However, any vibration sensor suitable for carrying out the invention may be employed.

Location and orientation of the accelerometer 80 is significant to the characteristics of the signal obtained. A vibration generated in one part of the motor 14 is transmitted through the solids separating the source from the accelerometer 80. Placement of the accelerometer 80 therefore defines transmission paths 88 and 89 through the motor 14 for transmission of vibrations from respective of the bearings 22, 24 to the accelerometer 80. The transmission paths 88 and 89 may have different transmission characteristics and/or different associated resonant frequencies, which would thereby provide a further difference in the vibration signal from each of the bearings 22, 24 which is received at the accelerometer 80.

The accelerometer 80 converts mechanical vibrations into analog electrical signals which are combined and delivered to the diagnostic module 44 via suitable connections such as a signal-bearing wire or optical fiber. As noted above, the accelerometer 80 is mounted on the motor 14, which requires access to the motor 14. In addition, the transmission paths 88 and 89 between the sources of the vibrations and the accelerometer 80 affect the amplitude and frequency distributions of the vibrations experienced by the accelerometer 80. Furthermore, analysis of the vibration signals based on comparisons of signals measured at different times is dependent on the ability to reproduce the precise location and direction of mounting of the accelerometer 80. Thus, the accelerometer 80 preferably is permanently mounted on the motor 14.

One advantage of positioning the diagnostic module 44 within close proximity to the motor 14 is that the length of wire from the accelerometer 80 to the diagnostic module 44 is minimized thereby minimizing the amount of ambient noise that may be introduced through the wires. Preferably, the diagnostic module 44 is positioned on the motor 14 such that the length of a respective sensor wire is less than three feet.

Figure 4:
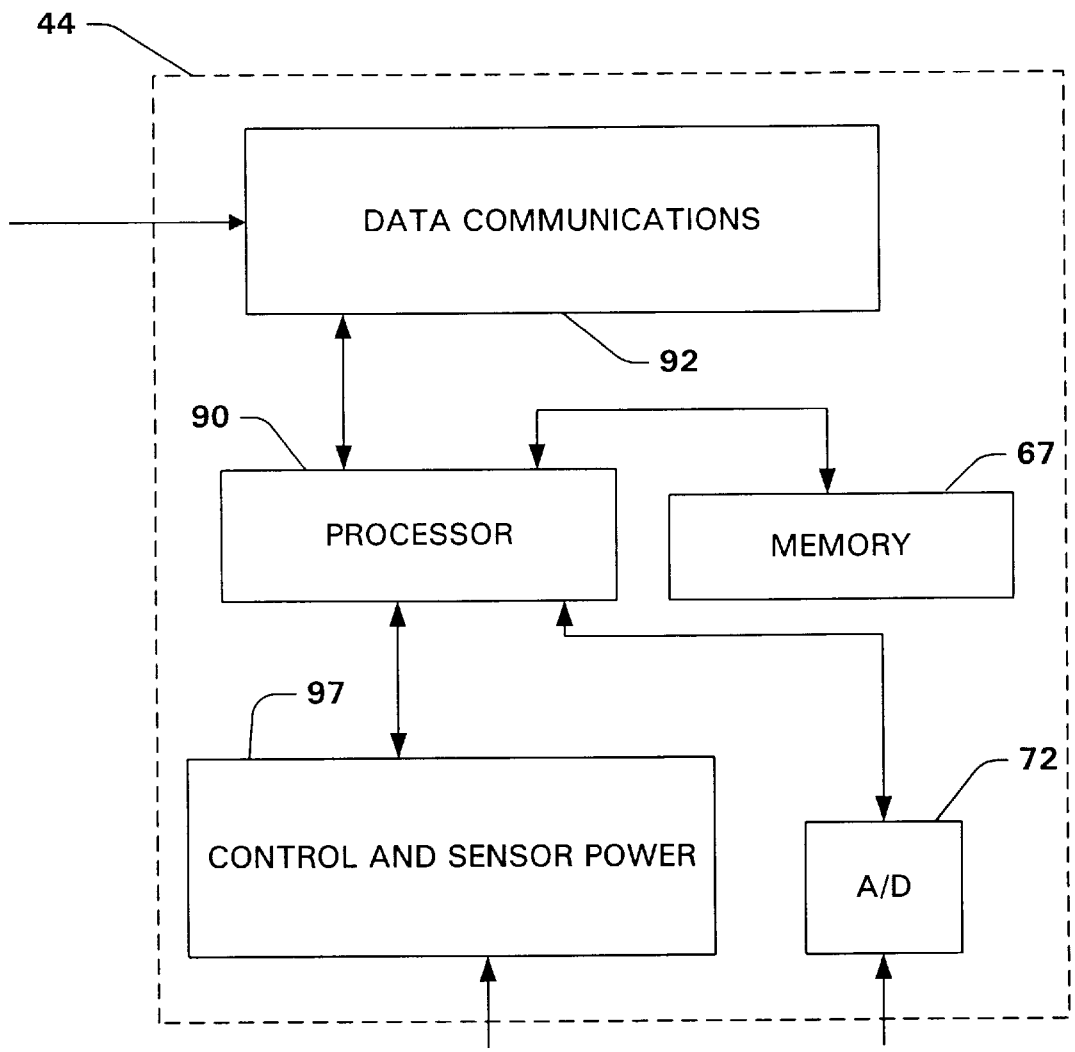
FIG. 4 is a functional schematic diagram of the diagnostic module of FIG. 1

The diagnostic module 44 includes an analog-to-digital (A/D) converter 72, as shown in FIG. 4, for converting the analog signal from the accelerometer 80 to a digital signal representative of the vibrations in the motor 14. It is to be appreciated that the A/D 72 may include various signal processing means (e.g., anti-aliasing filter) in order to suitably condition the incoming signals. The A/D converter 72 sends the digital signals to a processor or CPU 90 which may be a microprocessor. The processor 90 is responsible for controlling the general operation of the diagnostic module 44. The processor 90 is programmed to control and operate the various components within the diagnostic module 44 in order to carry out the various functions described herein. The processor 90 can be any of a plurality of suitable processors, such as the p24T, Pentium 50/75, Pentium 60/90, and Pentium 66/100, Pentium PRO and Pentium 2, Motorola MC68HC16Z1CFC16 and other similar and compatible processors. The manner in which the processor 90 can be programmed to carry out the functions relating to the present invention will be readily apparent to those having ordinary skill in the art based on the description provided herein and thus further discussion related thereto is omitted.

A memory 67 tied to the processor 90 also is included in the motor diagnostic module 44 and serves to store program code executed by the processor 90 for carrying out operating functions of the motor diagnostic module 44 as described herein. The memory 67 also serves as a storage medium for temporarily storing information such as vibration analysis data. The memory 67 also may include machine specific data (such as bearing critical frequencies and previously measured resonant frequency or frequencies of various vibration transmission paths) which is used to facilitate machine diagnosis.

The memory 67 includes read only memory (ROM) and random access memory (RAM). The ROM contains among other code the Basic Input-Output System (BIOS) which controls the basic hardware operations of the motor diagnostic module 44. The RAM is the main memory into which the operating system and application programs are loaded.

Power is provided to the processor 90 and other components forming the diagnostic module 44 from a control and sensor power system 97. However, it will be appreciated that such power could be obtained from the power source 38 themselves through power converting circuitry (not shown).

The diagnostic module 44 also includes a data communication system 92 which includes a data communication port and communications card (not shown), that are employed to interface the processor 90 with the interface device 50 and/or the host computer 66 via the network backbone 68. The communication system 92 preferably adheres to the RS232C or DeviceNet standard for communicating command and parameter information. However, any communication system suitable for carrying out the invention may be employed.

The invention may be used in a system which does not include an interface device 50 and host computer 66. All processing including data analyses and motor condition estimation and health determination could be accomplished by the processor 90 and the results transmitted to a PC or a control computer such as a programmable logic controller (PLC) (not shown). Furthermore, only one data link may be required. According to another embodiment, the processor 90 could be employed to simply trigger a single bit digital output which may be used to open a relay and turn the motor 14 off.

The processor 90 controls the signal sampling and digitizing rate as well as any buffering of the digitized signals of the vibration data that might be needed. The data collection rate is carried out, for example, at 26,203 samples per second over a period of 8 seconds. This data collection rate provides sufficient data upon which the processor 90 can generate a comprehensive frequency spectrum of the motor vibration signal suitable for analysis.

Figure 5:
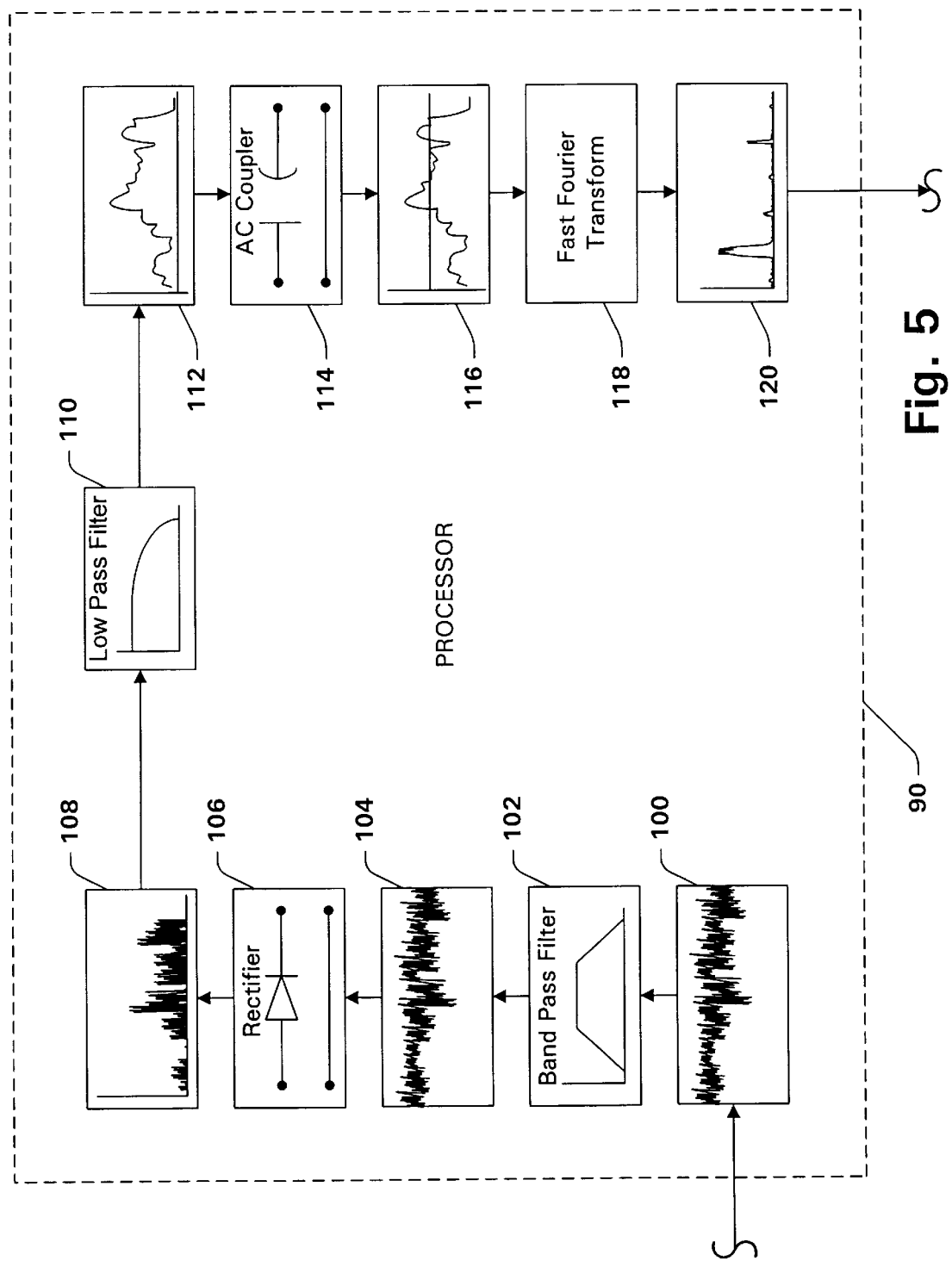
FIG. 5 is a functional block diagram illustrating the processing of vibration data by a processor of the diagnostic module.

As described above, the accelerometer 80 collects analog vibration data which is converted into a digital vibration signal by the A/D converter 72 which provides the digital vibration data to the processor 90. Referring hereafter also to FIG. 5, a functional block diagram represents the processing of vibration data by the processor 90 of the motor diagnostic module 44.

The processing performed on the vibration data by the processor 90 includes a process referred to as demodulation. One demodulation technique, sometimes referred to as enveloping, is performed by the processor 90 to synthesize the digital vibration data 100 into a form usable for failure analysis. The digital vibration data 100 enters the processor 90 and passes through a band pass filter 102 which removes frequencies outside the scope of interest and within the dynamic range of the processor 90 to form a filtered signal 104. The filtered signal 104 passes through a rectifier 106, for example a diode, which forms a rectified signal 108. The rectified signal 108 passes through a low pass filter 110 which removes the high frequencies to form a relatively low frequency signal 112. The low frequency signal 112 is passed through a capacitor 114 to produce a demodulated signal 116. A fast Fourier transform (FFT) is performed on the demodulated signal 116 by FFT operator 118 to produce a vibration spectrum 120. The FFT operator 118 includes commercially available fast Fourier transform software such as included in MATLAB by The Math Works. The FFTs of the vibration signal data are discretized over N number of points to facilitate processing. In the preferred embodiment, N=2,048, however, it will be appreciated that the FFTs of each signal may be discretized over any suitable number of points. The vibration spectrum 120 can be analyzed by the host computer 66 to determine the health of the motor 14.

Although the invention has been described with respect to obtaining FFTs of the vibration signals, other suitable techniques may be employed. For example, wavelet transforms may be taken of the sensor data. One advantage to using the wavelet transform is that the total size of the transform is a compact representation of the original signal and will require considerably less storage space than the original signal.

It is to be appreciated that prior to analyzing the vibration FFTs, it is desirable to know the motor speed in order to suitably interpret the FFT and detect defects and isolate particular bearing faults.

Figure 6:
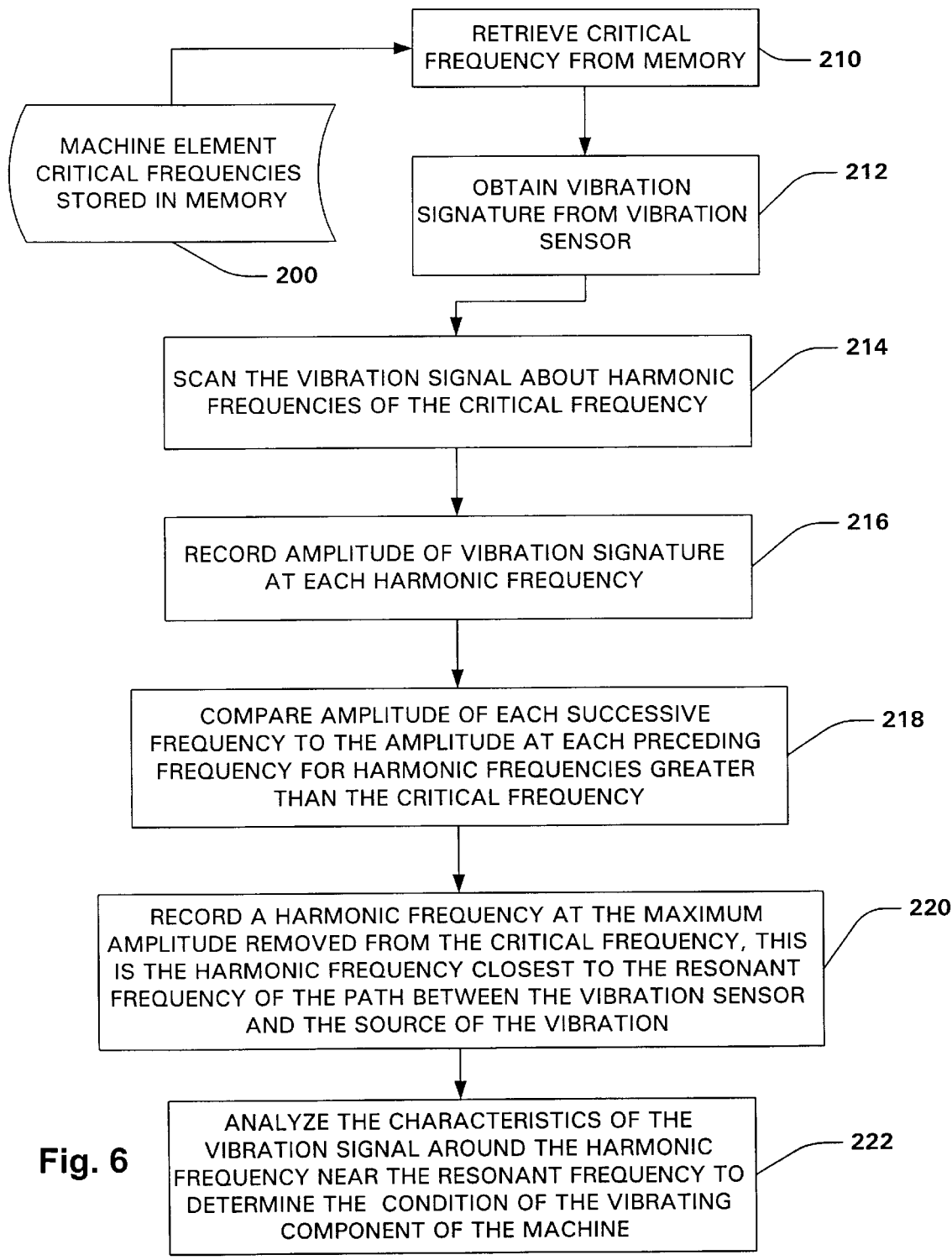
FIG. 6 is a flowchart illustrating a method of processing vibration data in accordance with the invention.
Figure 7:
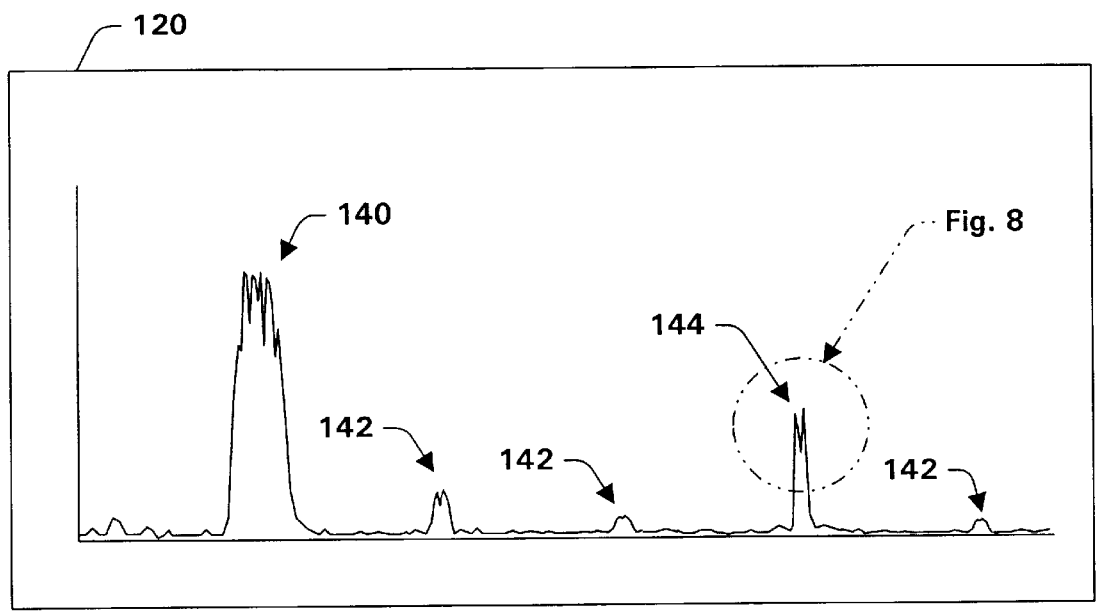
FIG. 7 is an illustration of a fast Fourier transform of vibration data in accordance with the method of FIGS. 5 and 6.

Referring now additionally to FIGS. 6 and 7, in the vibration spectrum 120 from the FFT operator 118 generally there is a lot of noise around the frequencies of interest 140. The sources of vibration, such as bearings, each produce vibrations at at least one frequency of interest, such as a bearing critical frequency. These frequencies of interest will vary between the two bearings due to the differences in vibration characteristics of the bearings, as explained above. The frequencies of interest 140 may be supplied by the manufacturer of the part which is the source of vibrations, and these frequencies may be entered into the memory 67 of the diagnostic module 44 using the keypad 60 of the display 50. Storage of the critical frequencies in memory is illustrated in step 200 of FIG. 6.

The amplitude is large near the frequencies of interest 140 but the signal is difficult to evaluate because there is a lot of noise around that frequency. Therefore, the processor 90 scans the vibration spectrum 120 around each harmonic of the frequency of interest, preferably up to at least about 10,000 Hz, step 214. For each harmonic the processor 90 records the amplitude, in step 216, and then compares the recorded amplitudes in step 218.

For higher frequency harmonics of the frequency of interest, the amplitude generally decreases from the amplitude at the frequency of interest 140. Harmonics 142 in FIG. 7 illustrate this generally decreasing amplitude. The amplitude suddenly increases above the noise at a harmonic 144, however, which is at or near the resonant frequency of one of the transmission paths from a vibration source to the accelerometer 80. The health of a particular component thus can be analyzed by considering the shape and magnitude of the vibration signals about the sampled frequencies near the harmonic 144, in step 222.

In a way the vibration source replaces the calibrated hammer blows. Thus the invention replaces the calibrated hammer with electronic devices and software which greatly facilitate the vibration analysis and improve its accuracy.

In addition, since the accelerometer 80 is permanently mounted, the resonant frequencies of the transmission paths from the accelerometer 80 to the sources of vibration, such as the bearings, do not change significantly over time. Thus the motor diagnostic module 44 can store in the memory 67 the resonant frequencies for various transmission paths to particular sources of vibration for future analysis. The determination of resonant frequencies from the accelerometer 80 to various vibration sources in the motor 14 may be done before the motor 14 leaves the factory. Once the resonant frequency has been stored in the memory 67, the vibration analysis can be accomplished much more rapidly since the processor 90 does not have to scan all of the harmonic frequencies. The processor 90 can go directly to the harmonic frequency near the resonant frequency.

Alternatively, if the frequency of interest is unknown, such as the bearing frequencies in a previously installed motor, a calibrated hammer (not shown) is used in a conventional manner to strike the motor adjacent a vibration source while the motor 14 is idle. From the frequency response measured by the accelerometer 80, the diagnostic module 44 calculates the approximate resonant frequency of the physical path between the impact point of the calibrated hammer and the accelerometer 80 in a conventional manner. Although not very precise, this approach narrows the frequency region that the diagnostic module 44 must scan.

When the motor 14 is operating, the accelerometer 80 measures the vibrations and the diagnostic module 44 scans the region about the approximate resonant frequency, recording amplitudes at a sequence of frequencies within that region and comparing the amplitudes at each frequency. Again, a sudden peak in amplitude indicates that a vibration source is generating vibrations, a harmonic of which is amplified about that frequency. In other words, at or near the frequency at which the amplified amplitude was measured there is a transmission path from one of the vibration sources to the accelerometer 80 that has a resonant frequency at the sampled frequency.

Figure 8:
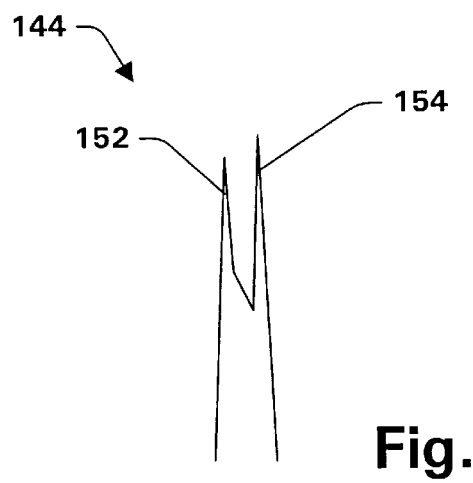
FIG. 8 is magnified view of the portion of FIG. 7 in the vicinity of a resonant frequency of the motor.

By examining the frequency associated with the peak in amplitude, the bearing which is the source of the sudden peak may be identified. As described earlier, the two bearings have different vibration characteristics, and therefore have different critical frequencies. The bearings also have harmonics at slightly different frequencies in the vicinity of the resonant frequency. This is illustrated in FIG. 8, which is a magnified view of a portion of the FFT shown in FIGS. 6 and 7. A first amplitude peak 152 is associated with the first bearing 22, for example, while a second amplitude peak 154 is associated with the second bearing 24. A sudden increase in amplitude at either of the peaks 152 or 154 would indicate a performance degradation in the bearing associated with that peak. Thus, the source of any irregular vibrations may be pinpointed to a single bearing, allowing maintenance efforts to be narrowly focused.

Once the processor 90 has processed all of the respective motor data, the processed data may be sent to the host computer 66 for analysis. The host computer 66 may then make determinations as to the health of the motor 14 and the health of its components, based on the data received from the diagnostic module 44. Accordingly, motor maintenance can be scheduled to correspond with the state of the motor 14. Additionally, the processed data can be compiled and stored for trend analysis and forecasting. Since the diagnostic module 44 is integrated with the motor 14, the data sampling rate can be substantially high thus providing accurate and up-to-date data relating to the health of the motor 14. However, as mentioned above, motor diagnosis, trend analysis, forecasting, etc. that could be performed by the host computer 66 alternatively may be performed directly by the diagnostic module 44.

The host computer 66 may utilize various analytical techniques such as those which generally fall under the category of conventional vibration analysis which have been proven to detect certain mechanical problems such as, for example, bearing failure, rotor problems, contamination from water or grit, holes in bearings, flat areas on bearings, broken or loose motor mounting, misalignment of motor shaft and load shaft, bent shafts, loose couplings, stator winding problems, fan problems, etc., as well as vibrations from other machine elements transmitted through the motor structure, such as gear mesh frequencies from a transmission connected between the motor 14 and the load 18.

Figure 9A:
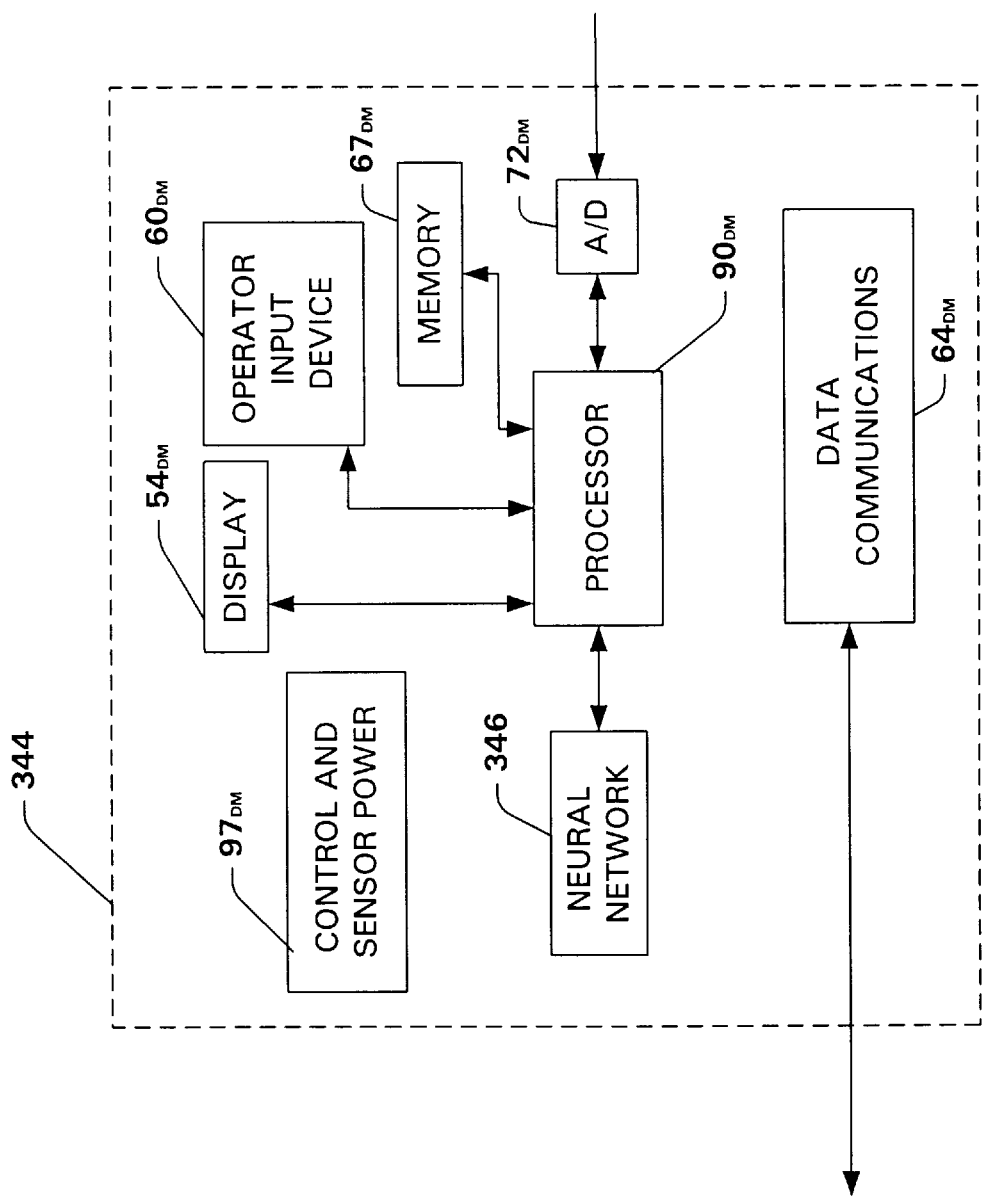
FIG. 9a is a functional schematic diagram of a diagnostic module including an operator interface device and employing a neural network in accordance with one aspect of the invention.
Figure 9B:
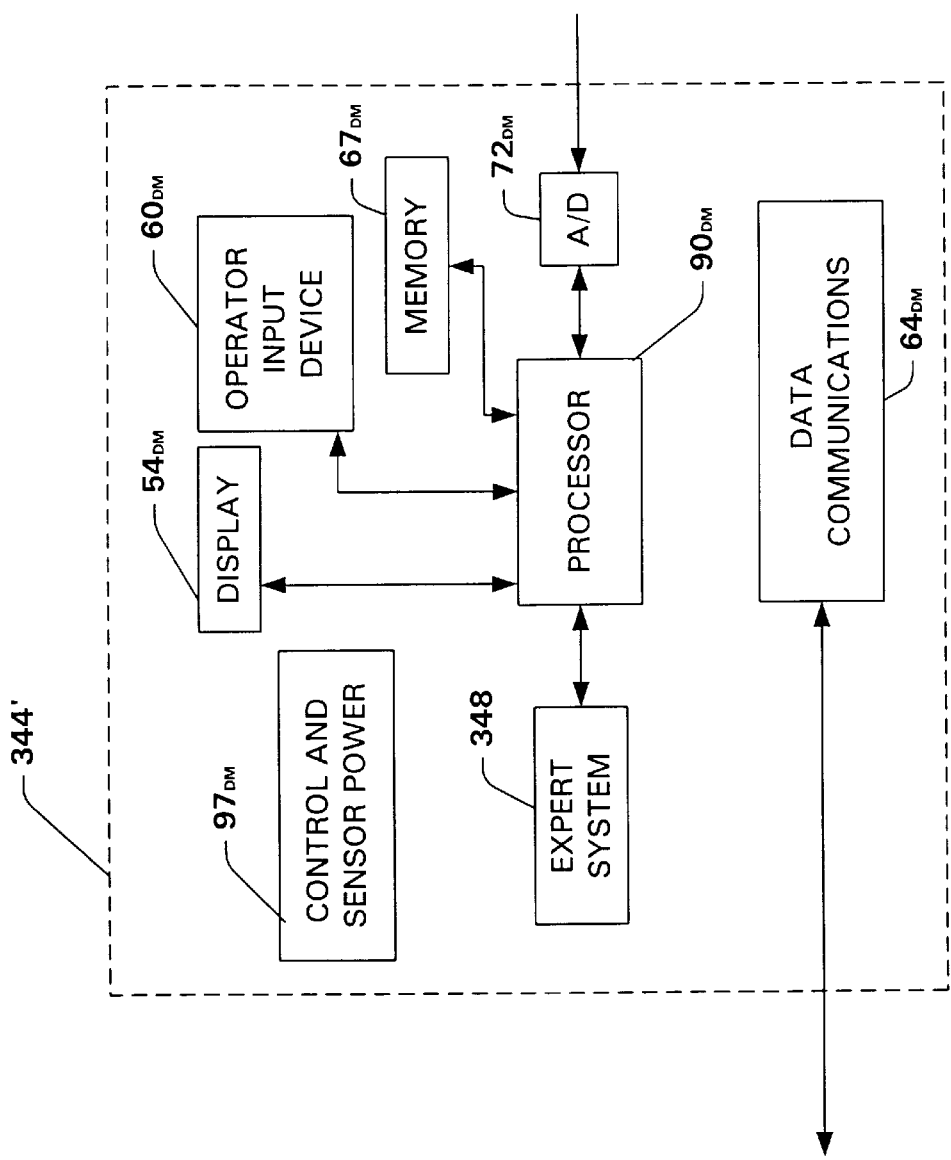
FIG. 9b is a functional schematic diagram of a diagnostic module including an operator interface device and employing an expert system in accordance with one aspect of the invention.

Turning now to FIG. 9a, another aspect of the invention is shown wherein a diagnostic module 344 functions to carry out the operations of the interface device 50 as well. The diagnostic module 344 includes essentially the same components as the diagnostic module 44 except that it also includes interface device 50 components as well. Accordingly, like parts between the diagnostic module 44 (FIG. 4) and the interface device 50 (FIG. 1) will share like reference numerals. However, the reference numerals of FIG. 9a for the diagnostic module 344 further include the subscript (DM) to designate that the component is associated with this particular embodiment. Further discussion as to the functions of the components is not repeated for the sake of brevity and to avoid redundancy. However, in this embodiment, the diagnostic module 344 further includes a neural network 346 which is employed to facilitate data analysis and processing. The use of neural networks for motor diagnostics is well known in the art and thus further discussion relating thereto is omitted. Alternatively, the invention may employ an expert system 348 in lieu of the neural network 346 for a diagnostic module 344' as shown in FIG. 9b.

The programming or training of neural networks involves supplying the input and corresponding output data of samples containing features, similar to those being searched for. The neural network in turn learns by adjusting weights assigned to each of the neurons. The weights and threshold values of the neurons determine the propagation of data through the network and thus provides a desired output based on a respective set of inputs. Although neural networks are accurate, and can become more accurate over time, they only can make a pseudo-binary type decision. On the other hand, an expert system provides classification based on inferences to derive more knowledge about a subject and in turn to employ logical reasoning in making a decision.

Expert systems are knowledge-based rule-driven systems. An expert system is employed in accordance with the invention by establishing a hardware or software based program which receives input from a knowledge expert as to the nature of the items being sought for classification—in this case motor state. That is, during the training, the expert system generates a rule or set of rules for each decision and stores given data into the knowledge base. The expert system also may employ an "inference" engine to derive more knowledge about the subject.

For further information regarding the detailed structure and operation of an exemplary diagnostic module which can be used to carry out the invention, reference may be had to commonly owned and copending U.S. patent application No. Ser. 08/988,177 which is incorporated herein by reference in its entirety.

Thus, the diagnostic module 44 is an integrated diagnostic device for determining the health of a machine. The integrated diagnostic module permits autonomous collection and processing of substantial amounts of data relevant to the health of a machine. Since the diagnostic module 44 is specific to a single machine, the accelerometer 80 can be permanently mounted to the machine and connected to the diagnostic module 44 to improve data reliability. Furthermore, since the diagnostic module is machine specific the data can be sampled continuously or at accelerated intervals which allows for more reliable trend analysis and forecasting (e.g., maintenance scheduling and failure prediction). Additionally, the close proximity of the diagnostic module 44 to the sensor 80 collecting data permits the use of short sensor wire lengths which reduce opportunities for the introduction of noise through the sensor wires. Moreover, the invention allows autonomous determination of the health of a machine using very sophisticated diagnostic techniques, particularly vibration signature analysis based on software scanning for transmission path resonance rather than requiring the use of a calibrated hammer.

The present invention has been described primarily within the context of employing a different number of ball bearings in at least two bearings, respectively, so as to provide for differing dynamic responses with respect to a common sensor. It is to be appreciated that the present invention may be employed to detect defects among bearings or other vibration generating components that are identical. For example, if a motor includes a front bearing and a rear bearing, which are identical in type, but situated along different physical paths from a common sensor the present invention may be employed to differentiate vibration signatures from the respective bearings, Each respective mechanical path to the common sensor will have a dynamic response (e.g., resonant frequency) which the present invention can identify in the manner described herein in order to determine an operating state of the bearings.

Although the invention has been shown and described with respect to a certain preferred embodiment or embodiments, equivalent alterations and modifications will occur to others skilled in the art upon reading and understanding this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the invention. In addition, while a particular feature of the invention may have been described above with respect to only one of several illustrated embodiments, such feature may be combined with one or more other features of the other embodiments, as may be desired and advantageous for any given or particular application.

What is claimed is:

1. A dynamoelectric machine diagnostic system, comprising:
   a vibration sensor to sense a vibration signature, the sensor mounted on a dynamoelectric machine having at least two bearings with unique vibration characteristics with respect to the sensor; and
   a processor operatively coupled to the sensor for receiving the vibration signature from the vibration sensor and evaluating the vibration signature in the vicinity of frequencies associated with the bearings to determine the condition of each of the bearings.

2. The diagnostic system of claim 1, wherein the processor converts received analog signals into digital signals.

3. The diagnostic system of claim 2, wherein the processor processes the vibration signature using a fast Fourier transform.

4. The diagnostic system of claim 1, further comprising a user interface device operatively coupled to the processor.

5. The diagnostic system of claim 1, wherein the vibration sensor is an accelerometer.

6. The diagnostic system of claim 1, wherein the processor evaluates the vibration signatures in the vicinity of resonant frequencies associated with transmission paths between the vibration sources and the vibration sensor.

7. A method for analyzing the health of a dynamoelectric machine, comprising:
   providing the machine with vibration-generating components, at least one of which has vibration characteristics different from others;
   obtaining a vibration signature from a vibration sensor connected to the machine;
   processing the vibration signature, the processing including scanning a frequency region adjacent to a resonant frequency of a vibration transmission path from one of the components to the vibration sensor for harmonic frequencies of the components; and
   determining the condition of the components from characteristics of the vibration signature at frequencies associated with each of the components.

8. The method of claim 7 wherein the processing further includes determining at least an approximate value of the resonant frequency of the vibration transmission path.

9. The method of claim 7, wherein the processing includes:
   determining at least one critical frequency for each of the components of the machine;
   identifying harmonic frequencies of respective of the critical frequencies;
   recording the amplitudes of the vibration signature at the harmonic frequencies; and
   comparing the recorded amplitudes to identify a sudden increase in amplitude of a harmonic frequency associated with one of the vibration-generating components.

10. A method for analyzing the health of a dynamoelectric machine, comprising:
    providing the machine with bearings, at least one of which has different vibration characteristics from the others;
    obtaining a vibration signature from a vibration sensor connected to the machine;
    processing the vibration signature; and
    determining the condition of the bearings from characteristics of the vibration signature at frequencies associated with each of the bearings.

11. A method for analyzing the health of a dynamoelectric machine, comprising:
    providing the machine with ball bearings, at least one of which has a different number of balls from the others;
    obtaining a vibration signature from a vibration sensor connected to the machine;
    processing the vibration signature; and
    determining the condition of the bearings from characteristics of the vibration signature at frequencies associated with each of the bearings.

12. A dynamoelectric machine diagnostic system, comprising:
    means for sensing vibrations, said means for sensing vibrations operative to sense vibrations from at least two bearings of a dynamoelectric machine; each bearing having a unique vibration characteristic with respect to the means for sensing vibrations; and
    means for processing the vibration characteristics, said means for processing the vibration characteristics being able to correspond the vibration characteristics to the respective bearings and to determine the health of each of the bearings.

13. The machine of claim 12 wherein the means for processing includes means for receiving a vibration signature from the vibration sensing means and evaluating vibration signature in the vicinity of a resonant frequency of at least one of the bearing.

* * * * *